(12) United States Patent
Schopman (10) Patent No.: US 10,232,411 B2
(45) Date of Patent: Mar. 19, 2019

(54) DEVICE FOR CLEANING A STYLUS OF A MEASURING PROBE

(71) Applicant: F.G.J. Lammertink Beheer B.V., Borne (NL)

(72) Inventor: Gerhardus Hendrikus Albertus Schopman, Borne (NL)

(73) Assignee: F.G.J. LAMMERTINK BEHEER B.V., Borne (NL)

( * ) Notice: Subject to any disclaimer, the term of this patent is extended or adjusted under 35 U.S.C. 154(b) by 0 days.

(21) Appl. No.: 15/033,341

(22) PCT Filed: Oct. 29, 2014

(86) PCT No.: PCT/NL2014/050749
§ 371 (c)(1),
(2) Date: Apr. 29, 2016

(87) PCT Pub. No.: WO2015/065183
PCT Pub. Date: May 7, 2015

(65) Prior Publication Data
US 2016/0263626 A1   Sep. 15, 2016

(30) Foreign Application Priority Data

Oct. 31, 2013   (NL) ..................................... 2011710

(51) Int. Cl.
*B08B 3/02*   (2006.01)
*B08B 5/02*   (2006.01)
(Continued)

(52) U.S. Cl.
CPC ................ *B08B 3/02* (2013.01); *B08B 3/022* (2013.01); *B08B 3/024* (2013.01); *B08B 5/02* (2013.01); *B08B 5/023* (2013.01); *G01B 5/012* (2013.01); *G01N 35/1004* (2013.01)

(58) Field of Classification Search
CPC ....................................................... B08B 3/022
See application file for complete search history.

(56) References Cited

U.S. PATENT DOCUMENTS 5,299,584 A   4/1994   Miyazaki et al.
9,063,107 B2   6/2015   Waterbury et al.
(Continued)

FOREIGN PATENT DOCUMENTS

DE   19610607 A1   9/1997
DE   10207499 A1   9/2003
(Continued)

OTHER PUBLICATIONS

International Preliminary Report on Patentability for International Application No. PCT/NL2014/050749 dated May 12, 2016.
(Continued)

*Primary Examiner* — Jason Y Ko
(74) *Attorney, Agent, or Firm* — Dinsmore & Shohl LLP (57) ABSTRACT

The invention relates to a device for cleaning a stylus (1) of a measuring probe (2), said device comprising: —a cleaning chamber (4) for accommodating said stylus (1) during a cleaning process, said cleaning chamber (4) comprising an opening (5) for introducing and removing said stylus (1) in and from said cleaning chamber (4); —supply means (7) for supplying a cleaning agent, for example a cleaning liquid or aerosol, and/or a drying agent, for example air, into said cleaning chamber (4) for cleaning and/or drying said stylus (1). The invention further relates to an assembly of such a device and a measuring machine.

18 Claims, 7 Drawing Sheets

(51) Int. Cl.
*G01B 5/012* (2006.01)
*G01N 35/10* (2006.01)

(56) References Cited

U.S. PATENT DOCUMENTS

| | | |
|---|---|---|
| 2004/0265185 A1 | 12/2004 | Kitagawa |
| 2008/0099057 A1 | 5/2008 | Dunfee et al. |
| 2009/0041622 A1 | 2/2009 | Maeda et al. |
| 2011/0283847 A1 | 11/2011 | Schreiber |
| 2014/0377132 A1 | 12/2014 | Shimase et al. |

FOREIGN PATENT DOCUMENTS

| | | |
|---|---|---|
| EP | 2025418 A1 | 2/2009 |
| JP | S62242858 A | 10/1987 |
| JP | H04323824 A | 11/1992 |
| JP | H08043009 A | 2/1996 |
| JP | 2003181388 A | 7/2003 |
| JP | 2004325117 A | 11/2004 |
| JP | 2005012197 A | 1/2005 |
| JP | 2006090945 A | 4/2006 |
| JP | 2007078435 A | 3/2007 |
| JP | 2009042067 A | 2/2009 |
| JP | 2010133727 A | 6/2010 |
| JP | 2013511721 A | 4/2013 |
| JP | 2013134142 A | 7/2013 |
| WO | 9701750 A1 | 1/1997 |
| WO | 20130099498 A1 | 7/2013 |

OTHER PUBLICATIONS

Japanese Office Action dated May 6, 2018, on Japanese Patent Application No. 2016-552398.

DEVICE FOR CLEANING A STYLUS OF A MEASURING PROBE

The invention relates to a device for cleaning a stylus of a measuring probe.

For measuring objects a measuring machine is used, which measuring machine comprises a measuring probe with a stylus. The measuring device may be any type of measuring device, for example a 3D measuring device. In particular, said measuring device may be part of a processing machine for measuring tools of the processing machine. If the stylus of the measuring probe is polluted, for example if dust or other particles attach thereto, measuring may not take place accurately.

It is an object of the invention to provide a device for cleaning a stylus of a measuring probe. In particular it may be an object of the invention to provide a device for cleaning a said stylus during a measurement process.

This object is achieved by a device according to the preamble, said device comprising:
- a cleaning chamber for accommodating said stylus during a cleaning process, said cleaning chamber comprising an opening for introducing and removing said stylus in and from said cleaning chamber, and
- supply means for supplying a cleaning agent, for example a cleaning liquid or aerosol, and/or a drying agent, for example air, into said cleaning chamber for cleaning and/or drying said stylus.

Said device according to the invention provides a cleaning chamber in which said stylus may be introduced via said opening. After introducing said stylus in said cleaning chamber preferably first a cleaning agent is supplied to said cleaning chamber for cleaning said stylus and preferably second a drying agent is supplied to said cleaning chamber for drying said stylus. After cleaning and/or drying said stylus said stylus may be removed from said cleaning chamber via said opening and a measuring process may be continued or started.

In an embodiment of the device according to the invention, said supply means comprise at least one supply opening or nozzle discharging into said cleaning chamber for supplying said cleaning agent and/or said drying agent into said cleaning chamber.

An advantage of the supply opening or nozzle is that said cleaning agent and/or said drying agent may be sprayed or blown in the direction of the stylus.

In a preferred embodiment of the device according to the invention said supply means comprise at least three said supply openings or nozzles.

An advantage of multiple supply openings or nozzles, in particular three or more supply openings or nozzles, is that said cleaning agent and/or said drying agent may be sprayed or blown in the direction of said stylus from different locations in the cleaning chamber, such that the whole outer surface of said stylus may be cleaned and/or dried. It is noted that said supply means may comprise any number of supply openings or nozzles, for example, three, four, five, six, seven, eight, nine, ten, or even more supply openings or nozzles, such that the stylus is sprayed or blown from a plurality of directions.

Preferably said supply openings or nozzles are spaced apart at substantial equal angular distances and are arranged for supplying said cleaning agent and/or said drying agent to a common location, in which common location said stylus may be located during cleaning and/or drying.

A stylus is a very sensitive measurement tool. Supplying the cleaning agent and/or drying agent to the stylus may cause the stylus to register incorrect measurement data influenced by said cleaning agent and/or said drying agent, which measurement data is thus not representative for the object that is being measured before and after cleaning of the stylus. If said stylus is held in said common location and receives said cleaning agent and/or said drying agent from said equally spaced supply openings or nozzles the different flows of cleaning agent and/or drying agent will balance out or will be in an equilibrium at the common location such that said stylus will not be influenced by the cleaning agent and/or drying agent and will not register incorrect measurement data. Such an embodiment of the device according to the invention has the advantage that the measuring process does not need to be stopped during cleaning of the stylus, because this will not influence the measurement process.

Said multiple supply openings or nozzles are preferably arranged at the same height or position as seen in a longitudinal direction of said cleaning chamber.

In another embodiment of the device according to the invention said supply opening or an outlet opening of said nozzle has a maximum diameter of 4 mm, preferably a maximum diameter of 1 mm, more preferably a maximum diameter of 0.5 mm, even more preferably a diameter of approximately 0.2 mm.

Such a relatively small supply opening or outlet opening of said nozzle provides the advantage that the cleaning agent and/or drying agent is sprayed or blown with relatively high pressure in the direction of the stylus.

It is noted that the diameter of the supply opening or outlet opening of said nozzle may have any size falling within said maximum ranges.

In yet another embodiment of the device according to the invention said device comprises a body surrounding said cleaning chamber, thereby defining a space between said body and said cleaning chamber, said body comprising an inlet opening for supplying said cleaning agent and/or said drying agent into said space, wherein said supply opening(s) or nozzle(s) connect said space to the inner space of said chamber.

In such an arrangement only one inlet opening has to be provided, independent of the number of supply openings or nozzles. The pressure of the cleaning agent and/or drying agent is hereby equal for all supply openings or nozzles. In particular in combination with the embodiment comprising equally spaced supply openings or nozzles this may support the effect of not influencing the stylus during cleaning and/or drying.

In yet another embodiment of the device according to the invention said device comprises a plurality of said cleaning chambers arranged at different positions, preferably in accordance with a shape of a plurality of styli of said measuring probe, each chamber comprising a said opening for introducing and removing said a stylus of said plurality of styli in and from said cleaning chamber.

By providing a plurality of cleaning chambers each comprising a said opening for introducing and removing a respective stylus of said plurality of styli of said probe in and from said cleaning chambers it is possible to clean a probe with multiple styli, for example arranged in a complex shape.

Said plurality of cleaning chambers may be provided in one body as well as in a plurality of bodies. The bodies of the plurality of bodies may be arranged in different positions and/or angles, for example in accordance with a shape of a plurality of styli of said measuring probe In yet another embodiment of the device according to the invention at least one recess is provided that extends from said cleaning chamber(s) for accommodating a pen like body that holds the stylus at its outer end.

In yet another embodiment of the device according to the invention said comprises a means for closing said opening or said plurality of openings for introducing and removing said stylus or said plurality of styli.

Said opening(s) may preferably be closed when no stylus or styli is/are present in said cleaning chamber. This embodiment of the device is in particular advantageous if said stylus or styli is part of a measuring machine that is part of a processing machine. During processing (waste) particles, such as shavings, dust, or the like, may be formed that may otherwise enter said opening(s) of said cleaning chamber, but are now prevented from entering the opening(s) by said closing means.

In yet another embodiment of the device according to the invention said device comprises at least one of:
- a pressure regulator for adjusting a pressure of said cleaning agent and/or said drying agent;
- a dispensing system for dispensing said cleaning agent, in particular for creating an aerosol of cleaning agent particles in air;
- a control unit for controlling said pressure regulator and/or said dispensing system and/or said supply means.

Practically said control unit is arranged for setting at least one of:
- a time period for supplying said cleaning agent and/or said drying agent to said cleaning chamber;
- a pressure of said pressure regulator;
- an amount of cleaning agent and/or drying agent to be supplied.

In yet another embodiment of the device according to the invention said device comprises a detector for detecting a presence of said stylus or said styli, wherein said control unit is arranged for controlling said pressure regulator and/or said dispensing system and/or said supply means in accordance with detecting the presence of said stylus or said styli.

In such an embodiment cleaning and/or drying may take place only after detecting the presence of said stylus or said styli, such that no cleaning agent and/or drying agent is wasted.

In yet another embodiment of the device according to the invention said pressure regulator regulates said pressure such that said pressure is between 0.5 bar to 6 bar, for example between 2 to 4 bar, for example between 2.5 bar to 3 bar.

The invention also relates to an assembly of a device according to any of the claims 1-13 and a measuring machine.

The measuring machine may be any type of measuring device, for example a 3D measuring device. In particular, said measuring device may be part of a processing machine for measuring tools of the processing machine. In particular said measuring machine comprises a measuring probe comprising a stylus or a plurality of styli.

In an embodiment of the assembly according to the invention said assembly comprises means for displacing said cleaning chamber and said stylus or styli with respect to each other.

The stylus or styli may be displaced for introduction into and removal from said cleaning chamber and/or for displacing back and forth in a particular direction said stylus or styli back and forth in a particular direction during cleaning. Alternatively said cleaning chamber(s) may be displaced for a same reason. In another embodiment said cleaning chamber(s) may be displaced in accordance with a shape or size of said stylus or styli.

It is preferred that said stylus or styli is not influenced during cleaning, such that cleaning may take place during a measuring process and said measuring process is not influenced nor has to be stopped. Alternatively, said measuring machine is arranged for temporarily stopping measuring or registration of measurement data during cleaning of said stylus or styli.

The invention further relates to an assembly according to claim 14, 15 or 16, comprising a plurality of said cleaning chambers arranged at different positions, preferably in accordance with a shape of a plurality of styli of said measuring probe, each chamber comprising a said opening for introducing and removing said a stylus of said plurality of styli in and from said cleaning chamber.

The invention will now be explained in more detail with reference to figures illustrated in a drawing, wherein:

FIGS. 1A-1C show a first embodiment of the device according to the invention and a stylus, wherein FIG. 1A is a perspective view, FIG. 1B is a longitudinal cross section and FIG. 1C is a perspective view at the height of the supply openings;

FIGS. 3A and 3B are a perspective view of a second embodiment of the device according to the invention comprising a closing means, wherein FIG. 3A shows the closing means in a first, closed position and FIG. 3B shows the closing means in a second, open position;

FIGS. 6A-6D are a perspective view of a fifth embodiment of the device according to the invention, wherein FIGS. 6A and 6B show the assembled device and FIGS. 6C and 6D show a body and a cleaning chamber, respectively;

In the figures same elements are denoted by same reference numerals.

Figure 1A:
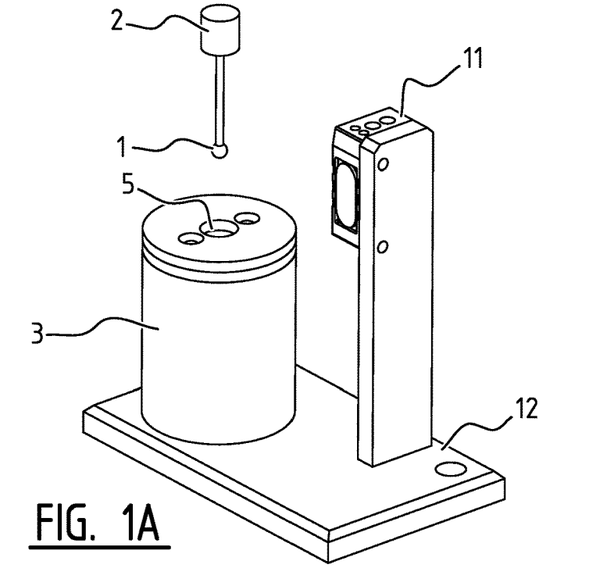
Figure 1B:
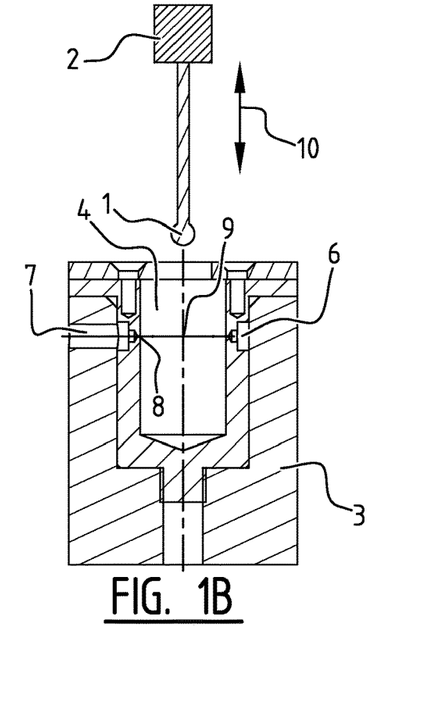
Figure 1C:
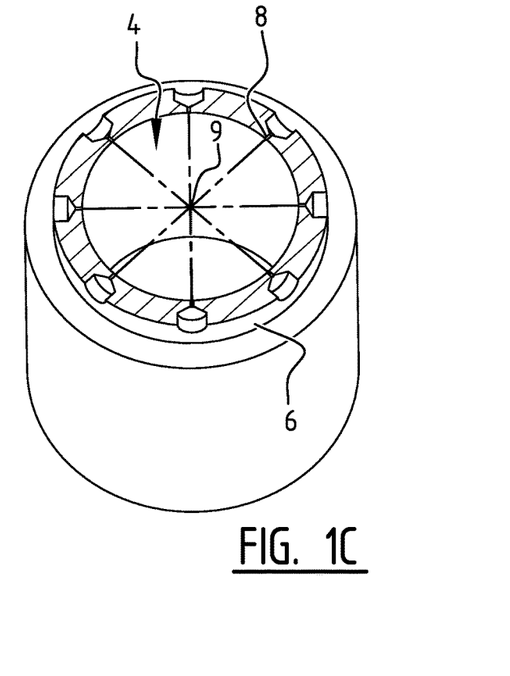

FIGS. 1A-1C show a device for cleaning a stylus 1 of a measuring probe 2 of a measuring machine (not shown). Said device comprises a body 3 with a cleaning chamber 4 for accommodating said stylus 1 during a cleaning process. The cleaning chamber 4 comprises an opening 5 for introducing and removing said stylus 1 in and from said cleaning chamber 3. Between the body 3 and the cleaning chamber 4 a space 6 is defined. To said space 6 an inlet opening 7 is connected for supplying a cleaning agent and/or a drying agent into said space 6. Said cleaning agent may be any suitable cleaning agent, such as a cleaning liquid, a cleaning gas or a cleaning aerosol in which cleaning liquid droplets are contained in a gas, for example air. Said drying agent may be any suitable drying agent, for example a drying gas, particularly air. Eight said supply openings 8 connect said space 6 to the inner space of said cleaning chamber 4 for supplying the cleaning agent and/or drying agent to said cleaning chamber 4. The eight supply openings 8 are spaced apart at substantial equal angular distances α, wherein α is 45° with eight supply openings 8, and are arranged for supplying said cleaning agent and/or said drying agent to a common location 9, in which common location 9 said stylus 1 may be located during cleaning and/or drying. The cleaning chamber 4 of the device of FIGS. 1A-1C is cylindrical, wherein the supply openings 8 are arranged tangentially in said cylindrical wall, such that the supply openings 8 are arranged for supplying the cleaning agent and/or drying agent in a radial direction, and wherein said stylus 1 is held in the center of the cleaning chamber 4 at the height of the supply openings 8. The applicant has found that in such a configuration with 8 equally distributed supply openings 8 spraying or blowing in radial direction and the stylus 1 held in the center the stylus 1 is not influenced by said cleaning agent and/or drying agent, such that the measuring process does not need to be stopped during cleaning.

Optionally, during cleaning and/or drying said stylus 1 may be moved back and forth in the direction 10 for exposing all parts of the stylus 1 to the cleaning agent and/or drying agent. Alternatively said cleaning chamber 4 may be moved back and forth in the direction 10. The direction 10 is parallel to the longitudinal direction of the cleaning chamber 4.

As is shown in FIG. 1B, the diameter of the supply opening 8 decreases in the direction of the cleaning chamber 4, thereby increasing the pressure and/or speed of the cleaning agent and/or drying agent. The diameter of the supply opening 8 at the entrance to the cleaning chamber 8 is 0.2 mm in the example of FIGS. 1A 1B, which has proven to provide a suitable pressure and/or speed for directing the cleaning agent and/or drying agent to the stylus 1 without influencing the stylus 1. It is noted, that any suitable diameter may be chosen.

As is shown in FIG. 1A, said device comprises a detector 11 for detecting a presence of said stylus 1. Upon detecting said stylus 1 a cleaning process may be initiated.

The body 3 and detector 11 are both mounted to a base 12. The base 12 may be arranged horizontally on a table or other support, or may be attached vertically to a support.

Figure 2:
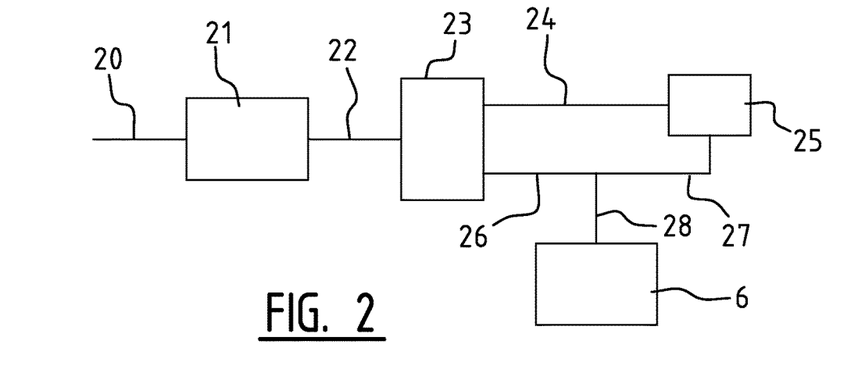
FIG. 2 is a flow diagram of supplying the device of FIG. 1 with a cleaning agent and/or drying agent.

FIG. 2 shows a flow diagram of supplying the device of FIG. 1 with said cleaning agent and/or said drying agent. A gas, for example air, is provided via a tube 20 or the like to a pressure regulator 21 for adjusting the pressure of the gas. The pressure of the gas is for example set between 0.5 bar to 6 bar, for example between 2 to 4 bar, for example between 2.5 bar to 3 bar. The gas under pressure is then supplied to a flow controller 23, which directs the gas to either tube 24 or the like or to tube 26 or the like. Tube 24 connects to a dispenser 25, in which dispenser 25 a cleaning agent is dispensed into said gas, such that cleaning liquid particles are contained in said gas. Said gas containing cleaning liquid particles is then fed to the space 6 and thereby the cleaning chamber via tube 27 and tube 28. Tube 26 directly connects to tube 28, such that the gas may be supplied to the space 6 and cleaning chamber 4 as said drying agent. A control unit is provided for controlling said pressure regulator 21, the amount of liquid dispensed in dispenser 25, and the flow controller 23 for controlling the time period for providing the gas to the space 6 first via the dispenser 25 for cleaning the stylus 1 and then directly via tubes 26, 28 for drying the stylus 1 after cleaning. For example, first the stylus 1 is cleaned for several seconds and then the stylus 1 is dried for several seconds. Said time periods may be suitably chosen and are not limited hereto.

Figure 3A:
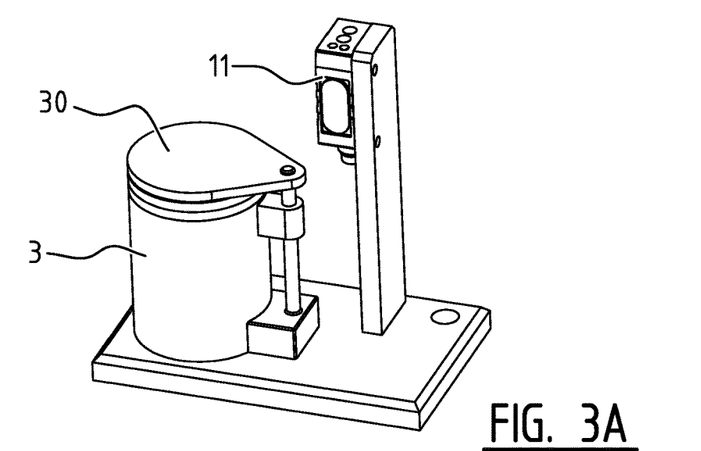
Figure 3B:
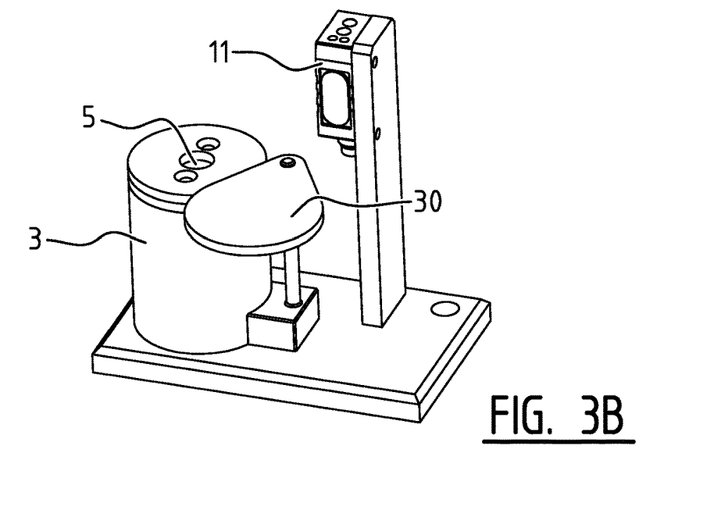

FIGS. 3A and 3B are a perspective view of a second embodiment of the device according to the invention. Said device according to the second embodiment differs only from the device according to the first embodiment in that the device comprises a closing valve 30 that is displaceable between a first, closed position as shown in FIG. 3A in which first position the valve 30 closes the opening 5 and a second, open position as shown in FIG. 3B in which second position the valve 30 does not close the opening 5. The valve 30 may be constantly held in its first position for closing the opening 5 and thereby protecting the cleaning chamber 4 from the outer environment, in particular protecting the cleaning chamber 4 from dust and other particles entering therein via the opening 5, and may be temporary displaced to its second position for releasing the opening 5 such that the stylus 1 may be introduced in the cleaning chamber 4 for cleaning the stylus 1. After cleaning the valve 30 is returned to its first position.

The valve 30 shown in FIGS. 3A and 3B rotates between its first and second position. It will be clear for the skill person that the valve may be displaced in any suitable way, for example by displacing the valve in translation. Instead of a valve any suitable closing means may be provided. A sealing may optionally be provided between said closing means or valve 30 and said opening 5.

It is noted that only the difference between the second embodiment of the device as shown in FIGS. 3A and 3B with respect to the first embodiment of the device as shown in FIGS. 1A 1C is described here. For a further description of the device according to FIGS. 3A and 3B the reader is referred to the description of FIGS. 1A-1C.

Figure 4:
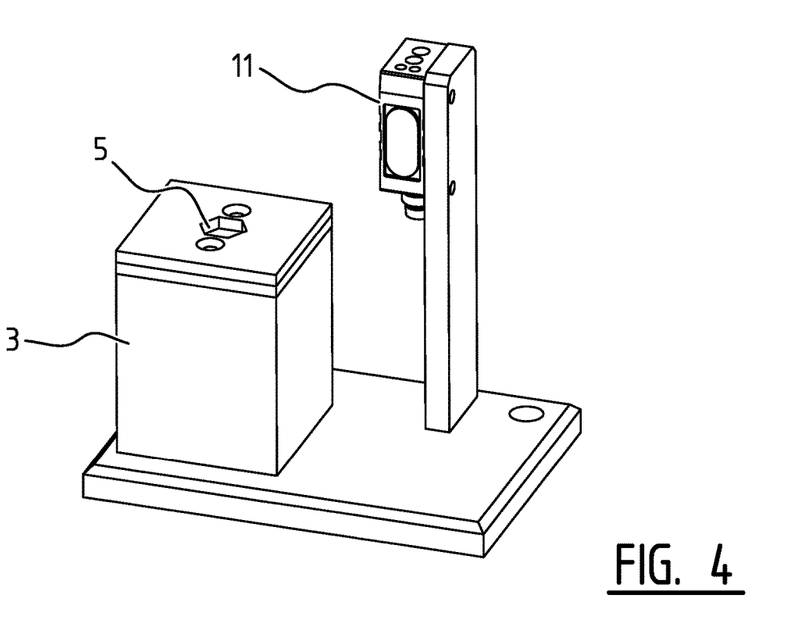
FIG. 4 is a perspective view of a third embodiment of the device according to the invention.

FIG. 4 is a perspective view of a third embodiment of the device according to the invention. Said device according to the third embodiment differs only from the device according to the first embodiment in that the cleaning chamber 4 and the opening 5 have a hexagonal cross section instead of a round cross section. In each of the six wall sections of the cleaning chamber 4 a supply opening is arranged, such that in total six supply openings are provided (not shown). The supply openings are preferably arranged at the same height in the longitudinal direction of the cleaning chamber 4, i.e. at the same longitudinal distance from the opening 5, and are preferably each arranged in the middle of each wall section seen in the transverse direction of the cleaning chamber 4 and wall section, such that the supply openings are spaced apart at equal angular distances α, wherein α is 60°. The supply openings are arranged for supplying said cleaning agent and/or said drying agent to a common location, which is the central longitudinal axis of the opening 5 and the cleaning chamber 4.

It is noted that instead of a hexagonal cross section each suitable polygonal cross section may be chosen. The supply openings may be provided in each wall section or in part of the wall sections.

It is further noted that only the difference between the third embodiment of the device as shown in FIG. 4 with respect to the first embodiment of the device as shown in FIGS. 1A-1C is described here. For a further description of the device according to FIG. 4 the reader is referred to the description of FIGS. 1A-1C.

Figure 5:
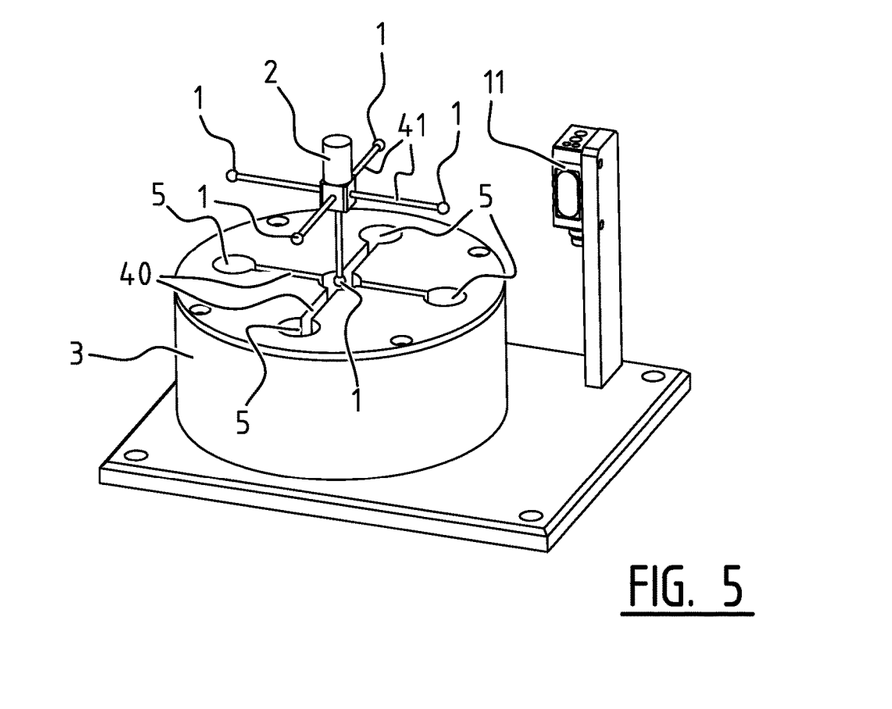
FIG. 5 is a perspective view of a fourth embodiment of the device according to the invention and a plurality of styli.

FIG. 5 is a perspective view of a fourth embodiment of the device according to the invention. Said device according to the fourth embodiment differs only from the device according to the first embodiment in that it comprises five openings 5 for receiving five styli 1 of a different type of measuring probe 2. The openings 5 are arranged in an upper surface of one body 3 in accordance with the shape of the styli 1 and are mutually connected via recesses 40, such that the five styli 1, which are held by pen like elements 41 at their outer ends, may simultaneously be introduced in a respective cleaning chamber 4 for cleaning the styli 1, preferably simultaneously. Each opening 5 provides entrance to a cleaning chamber 4, wherein each cleaning chamber 4 may comprise one or more supply openings for supplying the cleaning agent and/or drying agent. If a plurality of supply openings are provided to each cleaning chamber 4, the supply openings of each cleaning chamber 4 may be spaced apart at equal angular distances and may be arranged tangentially for supplying the cleaning agent and/or drying agent in radial direction.

It is noted that any suitable number of cleaning chambers 4 with openings 5 may be provided, for example in accordance with the shape of the styli 1 of the measuring probe 2.

It is further noted, that the plurality of cleaning chambers 4 provided in the one body 4 are mutually connected via recesses 40 and may therefore also be seen as one cleaning chamber 4.

It is further noted that only the difference between the fourth embodiment of the device as shown in FIG. 5 with respect to the first embodiment of the device as shown in FIGS. 1A-1C is described here. For a further description of the device according to FIG. 5 the reader is referred to the description of FIGS. 1A-1C.

FIGS. 6A-6D are a perspective view of a fifth embodiment of the device according to the invention. Said device according to the fifth embodiment differs from the device according to the first embodiment in that four recesses 40 are provided which extend from the central opening 5 in the upper surface of the body 3 to the outer, cylindrical circumference of the body 3. The opening 5 provides entrance to one central cleaning chamber 4 for receiving one of five styli 1 of the measuring probe 2 at a time. If the central, lower stylus 1 is introduced in the opening 5 in the upper surface of the body 3, the other four styli 1 extend outwards of the body 3 via the four circumferential recesses 40, which recesses 40 accommodate the pen like elements 41 of the probe 2 that hold the styli 1 at their outer ends (see FIG. 6A). Each of the other four styli 1, which are arranged in the same plane, may be introduced in the opening 5 via a respective recess 40, without the need to rotate the probe 2 with styli 1 (see FIG. 6B).

Figure 6A:
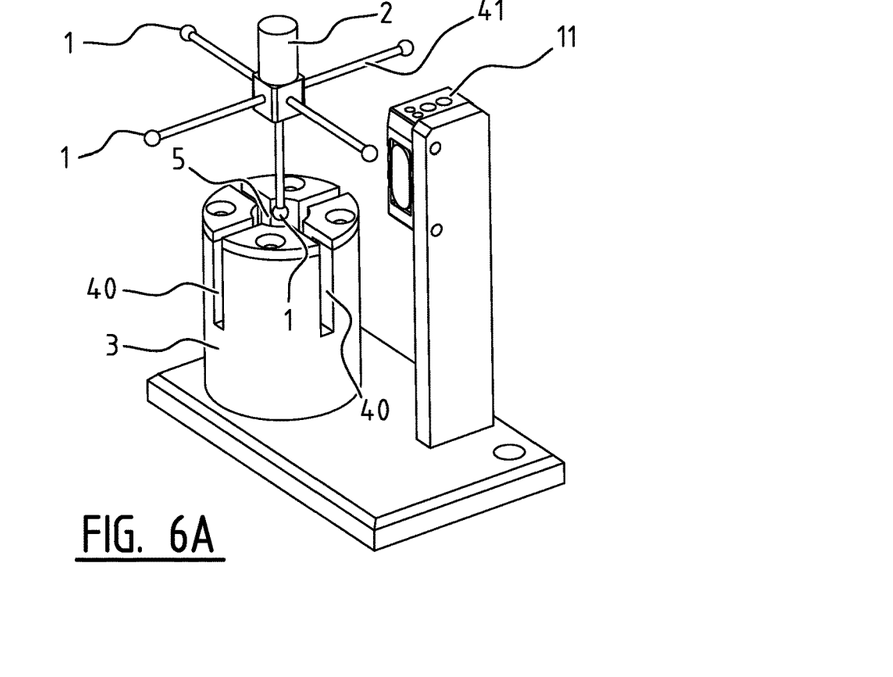
Figure 6B:
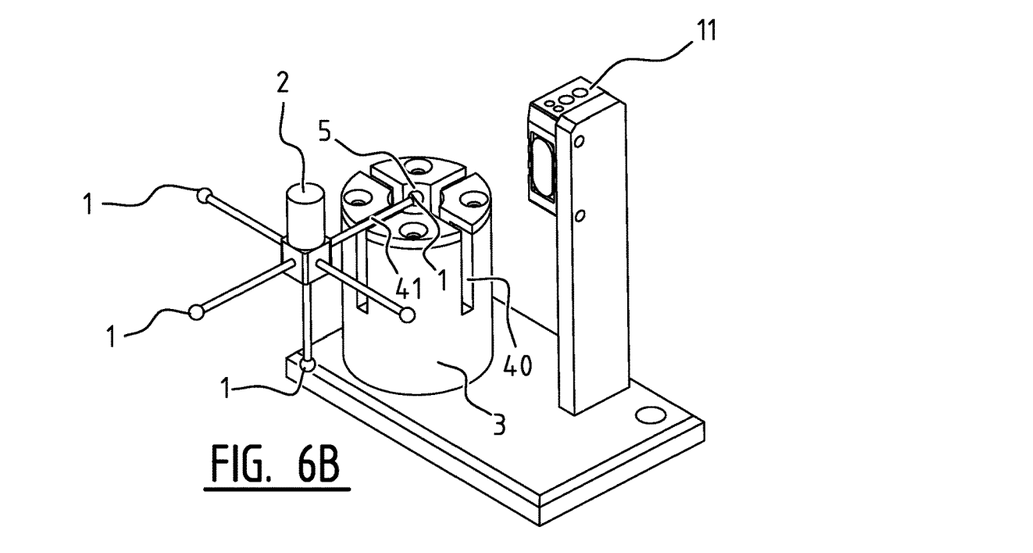
Figure 6C:
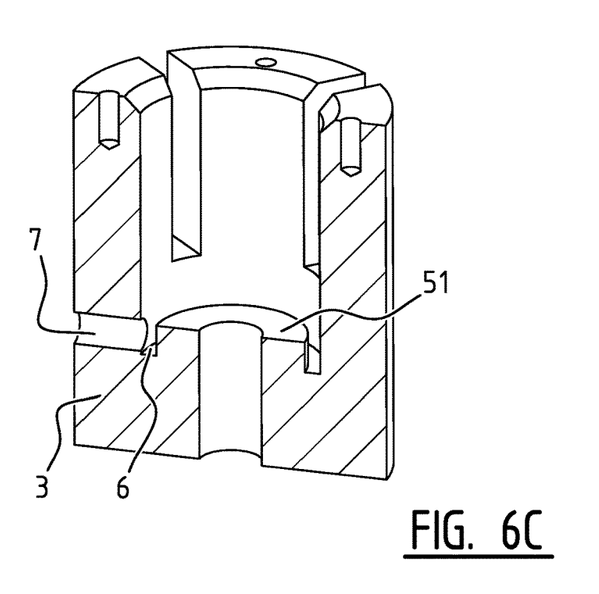
Figure 6D:
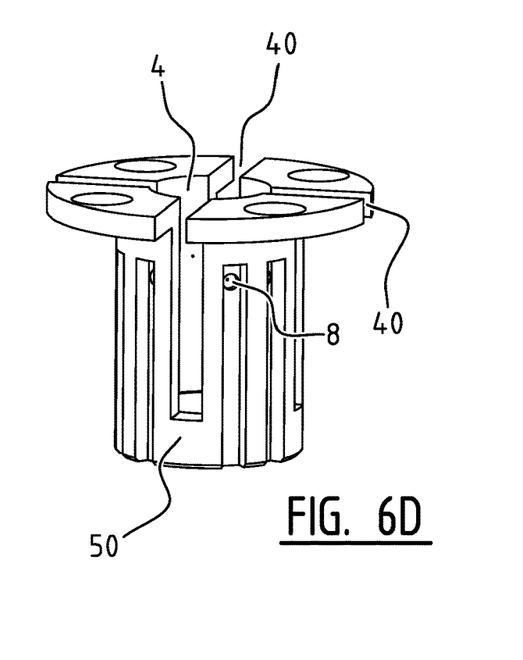

FIGS. 6C and 6D show the two elements forming the body 3 and cleaning chamber 4 in a disassembled state. FIG. 6D shows that each recess 40 comprises a sealing body 50 surrounding the recess 40 over a part of the outer periphery thereof. The sealing body 50 seals the space 6 shown in FIGS. 6C and 6D by being located against the inner wall of the body 3 and an upstanding annular protrusion 51 in the assembled state of FIG. 6A.

It is noted that only the differences between the fifth embodiment of the device as shown in FIGS. 6A-6D with respect to the first embodiment of the device as shown in FIGS. 1A-1C is described here. For a further description of the device according to FIGS. 6A-6D the reader is referred to the description of FIGS. 1A-1C.

Figure 7:
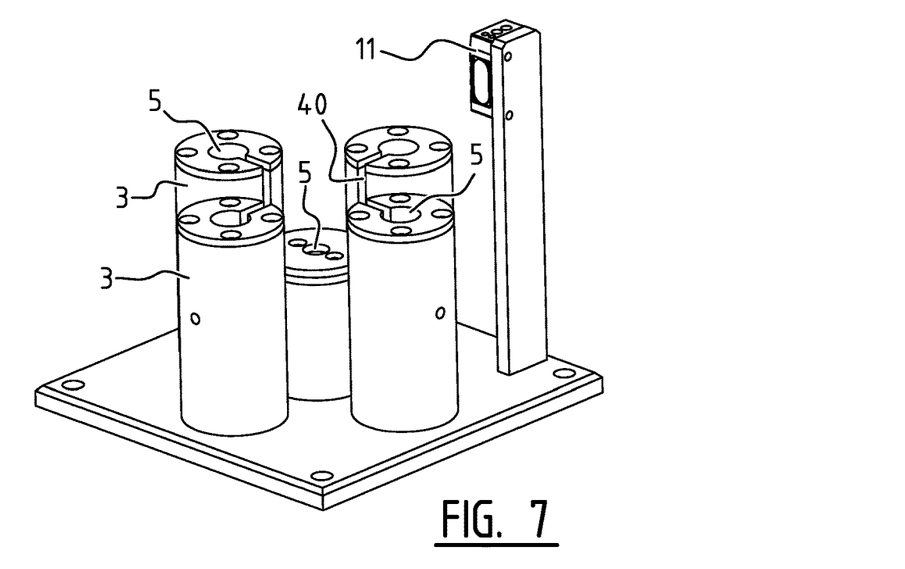
FIG. 7 is a perspective view of a sixth embodiment of the device according to the invention.

FIG. 7 is a perspective view of a sixth embodiment of the device according to the invention. Said device according to the sixth embodiment differs from the device according to the first embodiment in that it comprises five bodies 3, each body 3 comprising a cleaning chamber 4 and an opening 5. The embodiment of FIG. 7 is also suitable for cleaning the styli 1 of the probe 2 of FIGS. 5 and 6. The central, lower stylus 1 is introduced in the cleaning chamber 4 of the centrally arranged body 3, which is the same body 3 with cleaning chamber 4 as the one shown in FIGS. 1A-1C. The other four styli 1, that are located in the same plane, are introduced in a respective cleaning chamber 4 of a respective body 3 that is located around the centrally arranged body 3 via opening 5 and recess 40 for accommodating the pen like element 41 as shown in FIGS. 5 and 6. The bodies 3, each comprising a recess 40, are more or less similar to the body 3 shown in FIGS. 6A-6D, with the difference that it comprises only one recess 40. For a further description of those bodies 3 the reader is referred to the description of FIGS. 6A-6D. The bodies 3 are arranged such that each recess 30 is directed to the centrally arranged body 3, in accordance with the shape of the styli 1.

It is noted that only the differences between the sixth embodiment of the device as shown in FIG. 7 with respect to the first embodiment of the device as shown in FIGS. 1A-1C is described here. For a further description of the device according to FIG. 7 the reader is referred to the description of FIGS. 1A-1C.

Figure 8:
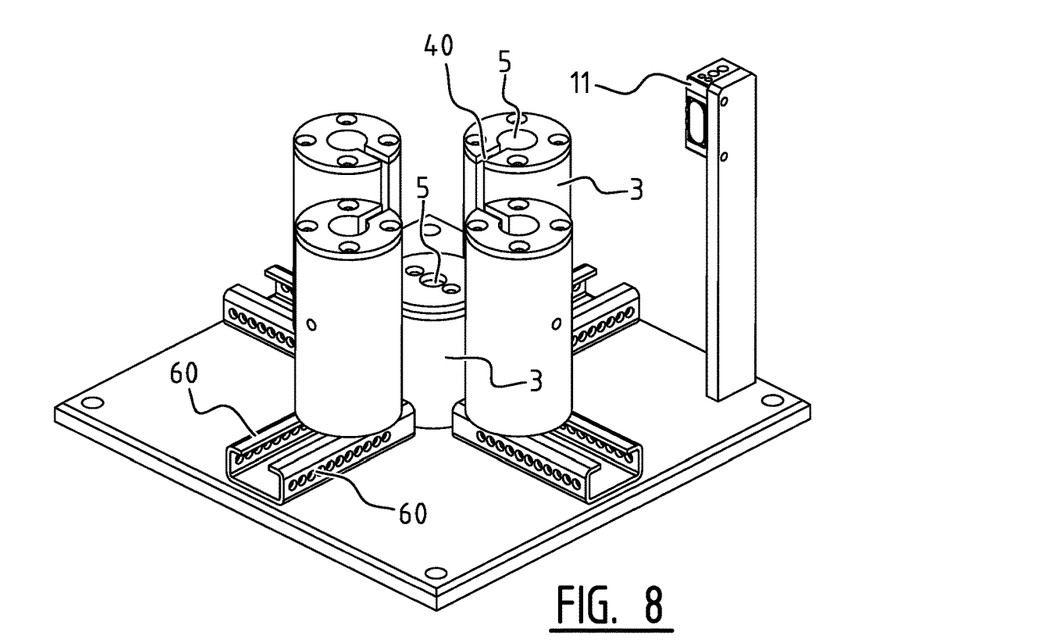
FIG. 8 is a perspective view of a seventh embodiment of the device according to the invention.

FIG. 8 is a perspective view of a seventh embodiment of the device according to the invention. Said device according to the seventh embodiment differs from the device according to the sixth embodiment in that the four outer bodies 3 are displaceable with respect to the centrally arranged body 3, such that the distance between each of the four outer bodies 3 and the centrally arranged body 3 is adjustable. The four outer bodies 3 are arranged on guiding rails 60 and displaceable along the length thereof. By adjusting the distance between each of the four outer bodies 3 and the centrally arranged body 3 it is possible to adapt the device to the size of a particular probe 2 with styli 1.

It is noted that only the difference between the seventh embodiment of the device as shown in FIG. 8 with respect to the sixth embodiment of the device as shown in FIG. 7 is described here. For a further description of the device according to FIG. 8 the reader is referred to the description of FIG. 7.

Figure 9:
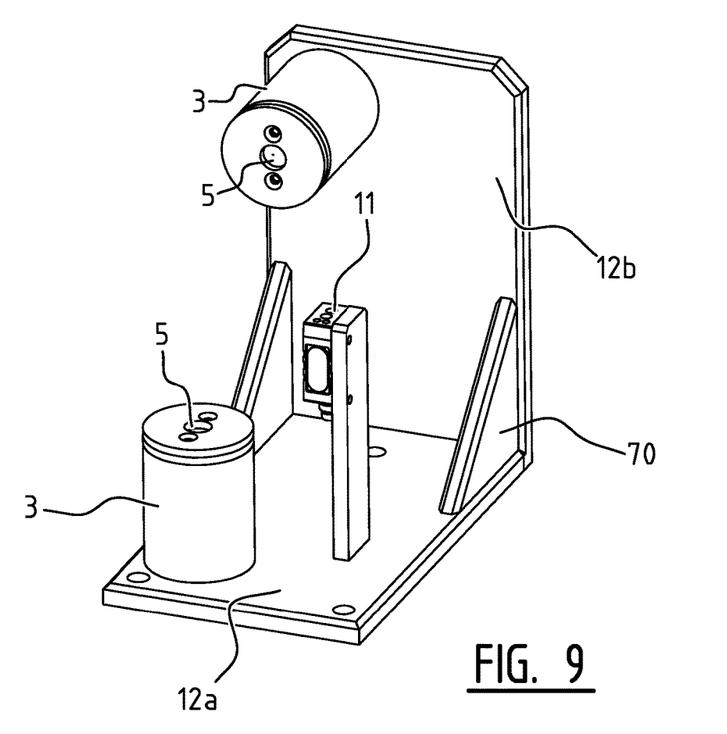
FIG. 9 is a perspective view of an eight embodiment of the device according to the invention.

FIG. 9 is a perspective view of an eight embodiment of the device according to the invention. Said device according to the eight embodiment differs from the device according to the first embodiment in that it comprises two bodies 3, each with a cleaning chamber 4 and an opening 5. The bodies 3 are each similar to the one shown in FIGS. 1A-1C. A first body 3 and the detector 11 are arranged on a base 12a, which configuration is more or less similar to the configuration shown in FIG. 1A. The second body 3 is arranged on a base 12b, which is attached to the base 12a under an angle of 90° with attachment means 70. The probe 2 with styli 1 of FIGS. 5 and 6 may be cleaned with the device according to FIG. 9 by rotating the styli 1 in only one plane, wherein the lower, central stylus 1 may be cleaned in the cleaning chamber 4 of the body 3 located on base 12a or 12b and wherein the other four styli 1 may be cleaned in the cleaning chamber 4 of the body 3 located on the other base 12b or 12a.

It is noted that only the differences between the eight embodiment of the device as shown in FIG. 9 with respect to the first embodiment of the device as shown in FIGS. 1A-1C is described here. For a further description of the device according to FIG. 9 the reader is referred to the description of FIGS. 1A-1C.

The invention is not restricted to the variants shown in the drawing, but it also extends to other preferred embodiments that fall within the scope of the appended claims.

The invention claimed is:

1. A measuring probe stylus cleaning device for cleaning a stylus of a measuring probe, said device comprising:
   a cleaning chamber for accommodating said stylus, said cleaning chamber comprising an opening for introducing and removing said stylus in and from said cleaning chamber;

supply means for supplying a cleaning agent or a drying agent into said cleaning chamber for cleaning or drying said stylus, wherein said supply means comprise at least three said supply openings or nozzles arranged along the side of the cleaning chamber at the same height;
a pressure regulator for adjusting a pressure of said cleaning agent or said drying agent; and
a control unit for controlling said pressure regulator;
wherein the diameter of the supply openings decreases in the direction of the cleaning chamber.

2. The device according to claim 1, wherein said supply means comprise at least one supply opening or nozzle discharging into said cleaning chamber for supplying said cleaning agent or said drying agent into said cleaning chamber.

3. The device according to claim 1, wherein said supply openings or nozzles are spaced apart at substantially equal angular distances and are arranged for supplying said cleaning agent or said drying agent to the common location, in which common location said stylus may be located during cleaning or drying.

4. The device according to claim 2, wherein said supply opening or an outlet opening of said nozzle has a diameter within a range of about 0.2 mm to about 4 mm.

5. The device according to claim 2, comprising a body surrounding said cleaning chamber, thereby defining a space between said body and said cleaning chamber, said body comprising an inlet opening for supplying said cleaning agent or said drying agent into said space, wherein said supply opening(s) or nozzle(s) connect said space to the inner space of said chamber.

6. The device according to claim 1, comprising a plurality of said cleaning chambers arranged at different positions, each chamber comprising a said opening for introducing and removing said a stylus of said plurality of styli in and from said cleaning chamber.

7. The device according to claim 1, comprising at least one recess extending from said cleaning chamber for accommodating a pen like body that holds the stylus at its outer end.

8. The device according to claim 1, wherein said control unit is arranged for setting at least one of:
a time period for supplying said cleaning agent or said drying agent to said cleaning chamber; and
an amount of cleaning agent or drying agent to be supplied.

9. The device according to claim 1, comprising a detector for detecting a presence of said stylus or said styli, the detector positioned externally from the cleaning chamber, wherein said control unit is responsive to the detector and is configured to control said pressure regulator and/or said supply means in response to the detector detecting the presence of said stylus or said styli.

10. The device according to claim 1, wherein said pressure regulator regulates said pressure such that said pressure is between 0.5 bar to 6 bar.

11. An assembly of a measuring probe stylus cleaning device according to claim 1 and a 3D measuring machine of a processing machine for measuring tools of the processing machine, said measuring machine comprising a measuring probe comprising a stylus or a plurality of styli to be cleaned.

12. An assembly according to claim 11, comprising means for displacing said cleaning chamber and said stylus or styli with respect to each other.

13. The assembly according to claim 11, wherein said measuring machine is arranged for temporarily stopping measuring or registration of measurement data during cleaning of said stylus or styli.

14. The assembly according to claim 11, comprising a plurality of said cleaning chambers arranged at different positions, in accordance with a shape of a plurality of styli of said measuring probe, each chamber comprising a said opening for introducing and removing said a stylus of said plurality of styli in and from said cleaning chamber.

15. The device according to claim 5, wherein the body and the cleaning chamber therein are displaceable between multiple positions.

16. The device of claim 1, further comprising a dispensing system that dispenses said cleaning agent by creating an aerosol of cleaning agent particles in air.

17. The device according to claim 1, further comprising a closing valve for closing said opening or said plurality of openings for introducing and removing said stylus or said plurality of styli.

18. A measuring probe stylus cleaning device for cleaning a stylus of a measuring probe, said device comprising:
a cleaning chamber for accommodating said stylus, said cleaning chamber comprising an opening for introducing and removing said stylus in and from said cleaning chamber;
supply means for supplying a cleaning agent or a drying agent into said cleaning chamber for cleaning or drying said stylus, wherein said supply means comprise at least three said supply openings or nozzles arranged along the side of the cleaning chamber at the same height;
a pressure regulator for adjusting a pressure of said cleaning agent or said drying agent;
a control unit for controlling said pressure regulator, wherein said pressure regulator regulates said pressure such that said pressure is between 0.5 bar to 6 bar; and
a detector for detecting a presence of said stylus or said styli, the detector positioned externally from the cleaning chamber, wherein said control unit is responsive to the detector and is configured to control said pressure regulator and/or said supply means in response to the detector detecting the presence of said stylus or said styli;
wherein the diameter of the supply openings decreases in the direction of the cleaning chamber.

* * * * *